United States Patent
Coe et al.

(10) Patent No.: US 7,499,759 B2
(45) Date of Patent: Mar. 3, 2009

(54) DISTAL OR PROXIMAL FIXATION OF OVER-THE-TETHER MYOCARDIAL LEADS

(75) Inventors: M. Sean Coe, Plymouth, MN (US); Ronald W. Heil, Jr., Roseville, MN (US); Peter T. Kelley, Buffalo, MN (US); Jason Alan Shiroff, Shoreview, MN (US); Randy W. Westlund, River Falls, WI (US); Donald F. Palme, II, Princeton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 288 days.

(21) Appl. No.: 10/972,298

(22) Filed: Oct. 22, 2004

(65) Prior Publication Data

US 2005/0137674 A1 Jun. 23, 2005

Related U.S. Application Data

(60) Provisional application No. 60/514,665, filed on Oct. 27, 2003, provisional application No. 60/514,714, filed on Oct. 27, 2003, provisional application No. 60/514,713, filed on Oct. 27, 2003, provisional application No. 60/514,037, filed on Oct. 24, 2003, provisional application No. 60/514,042, filed on Oct. 24, 2003, provisional application No. 60/514,039, filed on Oct. 24, 2003, provisional application No. 60/514,146, filed on Oct. 24, 2003, provisional application No. 60/514,038, filed on Oct. 24, 2003.

(51) Int. Cl.
A61N 1/05 (2006.01)

(52) U.S. Cl. ............... 607/126; 607/129; 607/130
(58) Field of Classification Search ............ 607/116, 607/119, 122, 126, 128–130; 606/129
See application file for complete search history.

(56) References Cited

U.S. PATENT DOCUMENTS 3,244,174 A 4/1966 Wesbey et al.

(Continued)

FOREIGN PATENT DOCUMENTS

DE 2219044 11/1972

(Continued)

OTHER PUBLICATIONS

Assad et al., New Lead for In-Utero Pacing for Fetal Congenital Heart Block, Journal of Thoracic and Cardiovascular Surgery, Jul. 2003.

(Continued)

*Primary Examiner*—Carl H Layno
*Assistant Examiner*—Eugene T Wu
(74) *Attorney, Agent, or Firm*—Faegre & Benson LLP

(57) ABSTRACT

The present invention is a myocardial lead attachment system for securing a lead within the myocardium. The attachment system includes an anchor configured to engage the heart, a tether coupled to the anchor and a lead body. The lead body has a proximal end, a distal end, a lumen for accepting the tether and a lock housing in the lumen. A lock structure is on the tether and mates with the lock housing and restrains motion of the lead with respect to the tether in either of a proximal or a distal direction.

16 Claims, 9 Drawing Sheets

U.S. PATENT DOCUMENTS

| | | | |
|---|---|---|---|
| 3,474,791 A | 10/1969 | Bentov | |
| 3,737,579 A | 6/1973 | Bolduc | |
| 4,142,530 A * | 3/1979 | Wittkampf | 607/116 |
| 4,161,952 A * | 7/1979 | Kinney et al. | 607/122 |
| 4,258,724 A | 3/1981 | Balat et al. | |
| 4,341,226 A | 7/1982 | Peters | |
| 4,355,642 A | 10/1982 | Alferness | |
| 4,378,023 A | 3/1983 | Trabucco | |
| 4,444,206 A | 4/1984 | Gold | |
| 4,444,207 A | 4/1984 | Robicsek | |
| 4,475,560 A | 10/1984 | Tarjan et al. | |
| 4,628,944 A | 12/1986 | MacGregor et al. | |
| 4,633,880 A | 1/1987 | Osypka et al. | |
| 4,735,205 A | 4/1988 | Chachques et al. | |
| 4,827,940 A | 5/1989 | Mayer et al. | |
| 4,991,578 A | 2/1991 | Cohen | |
| 5,009,229 A | 4/1991 | Grandjean et al. | |
| 5,217,027 A | 6/1993 | Hermens | |
| 5,241,957 A | 9/1993 | Camps et al. | |
| 5,246,014 A * | 9/1993 | Williams et al. | 607/122 |
| 5,300,107 A | 4/1994 | Stokes et al. | |
| 5,314,462 A * | 5/1994 | Heil et al. | 607/128 |
| 5,314,463 A | 5/1994 | Camps et al. | |
| 5,318,543 A | 6/1994 | Ross et al. | |
| 5,327,909 A | 7/1994 | Kiser et al. | |
| 5,336,252 A | 8/1994 | Cohen | |
| 5,350,419 A | 9/1994 | Bendel et al. | |
| 5,385,579 A | 1/1995 | Helland | |
| 5,423,876 A | 6/1995 | Camps et al. | |
| 5,693,081 A | 12/1997 | Fain et al. | |
| 5,716,392 A | 2/1998 | Bourgeois et al. | |
| 5,755,767 A | 5/1998 | Doan et al. | |
| 5,807,399 A * | 9/1998 | Laske et al. | 607/126 |
| 5,836,994 A | 11/1998 | Bourgeois | |
| 5,871,532 A | 2/1999 | Schroeppel | |
| 6,041,258 A | 3/2000 | Cigaina et al. | |
| 6,173,206 B1 | 1/2001 | Shchervinsky | |
| 6,304,786 B1 | 10/2001 | Heil, Jr. et al. | |
| 6,360,129 B1 | 3/2002 | Ley et al. | |
| 6,360,130 B1 | 3/2002 | Duysens et al. | |
| 6,370,434 B1 | 4/2002 | Zhang et al. | |
| 6,405,091 B1 | 6/2002 | Vachon et al. | |
| 6,434,431 B1 | 8/2002 | Camps et al. | |
| 6,459,937 B1 | 10/2002 | Morgan et al. | |
| 6,473,654 B1 | 10/2002 | Chinn | |
| 6,491,707 B2 | 12/2002 | Makower et al. | |
| 6,510,332 B1 | 1/2003 | Greenstein | |
| 6,512,958 B1 | 1/2003 | Swoyer et al. | |
| 6,567,704 B2 | 5/2003 | Sundquist et al. | |
| 6,613,062 B1 | 9/2003 | Leckrone et al. | |
| 6,626,919 B1 | 9/2003 | Swanstrom | |
| 6,671,553 B1 | 12/2003 | Helland et al. | |
| 6,671,561 B1 | 12/2003 | Moaddeb | |
| 6,842,648 B2 | 1/2005 | Partridge et al. | |
| 6,941,174 B2 | 9/2005 | Shchervinsky | |
| 2001/0000349 A1* | 4/2001 | Coe et al. | 607/119 |
| 2001/0039436 A1 | 11/2001 | Frazier et al. | |
| 2002/0013571 A1 | 1/2002 | Goldfarb et al. | |
| 2002/0072787 A1 | 6/2002 | Partridge et al. | |
| 2002/0077685 A1 | 6/2002 | Sundquist et al. | |
| 2002/0123785 A1 | 9/2002 | Zhang et al. | |
| 2002/0183818 A1* | 12/2002 | Williams et al. | 607/122 |
| 2003/0023295 A1 | 1/2003 | Osypka | |
| 2003/0028232 A1 | 2/2003 | Camps et al. | |
| 2003/0045919 A1 | 3/2003 | Swoyer et al. | |
| 2003/0055463 A1 | 3/2003 | Gordon et al. | |
| 2003/0125787 A1 | 7/2003 | Shchervinsky | |
| 2003/0204231 A1 | 10/2003 | Hine et al. | |
| 2004/0010282 A1 | 1/2004 | Kusleika | |
| 2004/0015193 A1 | 1/2004 | Lamson et al. | |
| 2004/0054388 A1 | 3/2004 | Osypka | |
| 2004/0260371 A1* | 12/2004 | Greenland et al. | 607/116 |
| 2005/0033394 A1 | 2/2005 | Seifert et al. | |
| 2005/0033395 A1* | 2/2005 | Seifert et al. | 607/126 |
| 2005/0033396 A1 | 2/2005 | Osypka | |
| 2005/0070986 A1 | 3/2005 | Tockman et al. | |
| 2005/0113900 A1 | 5/2005 | Shiroff et al. | |
| 2005/0113901 A1 | 5/2005 | Coe et al. | |

FOREIGN PATENT DOCUMENTS

| | | |
|---|---|---|
| DE | 4425195 | 4/2003 |
| EP | 1000834 | 5/2000 |
| EP | 1025802 A | 8/2000 |
| GB | 2025236 A | 1/1980 |
| WO | 2004/091716 | 10/2004 |
| WO | 2005/028023 | 3/2005 |

OTHER PUBLICATIONS

Epstein et al., Long-Term Performance of Bipolar Epicardial Atrial Pacing Using an Active Fixation Bipolar Endocardial Lead, PACE, Apr. 1998.

Karpawich et al., Improved Epimyocardial Pacing, PACE, Nov. 1994.

Worley et al., Construction of a Multipolar Electrode System Referenced and Anchored to Endocardium for Study of Arrhythmias, American Physiological Society, 1986.

German Office Action citing prior art to related German Patent Application and English translation thereof.

Office Action received in related case U.S. Appl. No. 10/972,049, mailed Jul. 24, 2006.

Office Action received in related case U.S. Appl. No. 10/972,049, mailed Jan. 11, 2007.

Office Action received in related case U.S. Appl. No. 10/971,549, mailed Feb. 2, 2007.

Office Action received in related case U.S. Appl. No. 10/821,421, mailed May 25, 2006.

Office Action received in related case U.S. Appl. No. 10/821,421, mailed Nov. 24, 2006.

Office Action received in related case U.S. Appl. No. 10/821,421, mailed Mar. 22, 2007.

International Search Report and Written Opinion of International Application No. PCT/2004/010907, filed Apr. 9, 2004, both mailed Sep. 16, 2004.

International Search Report and Written Opinion of International Application No. PCT/US2004/035172, filed Oct. 22, 2004, both mailed Jan. 31, 2004.

Office Action received in related case U.S. Appl. No. 10/971,577, mailed Aug. 7, 2007.

Office Action received in related case U.S. Appl. No. 10/971,549, mailed Jul. 27, 2007.

Office Action received in related case U.S. Appl. No. 10/972,049, mailed Jul. 2, 2007.

Agreement between Cardiac Pacemakers, Inc. and Dr. Osypka GmbH, dated Aug. 26, 2002, 2 pp.

* cited by examiner

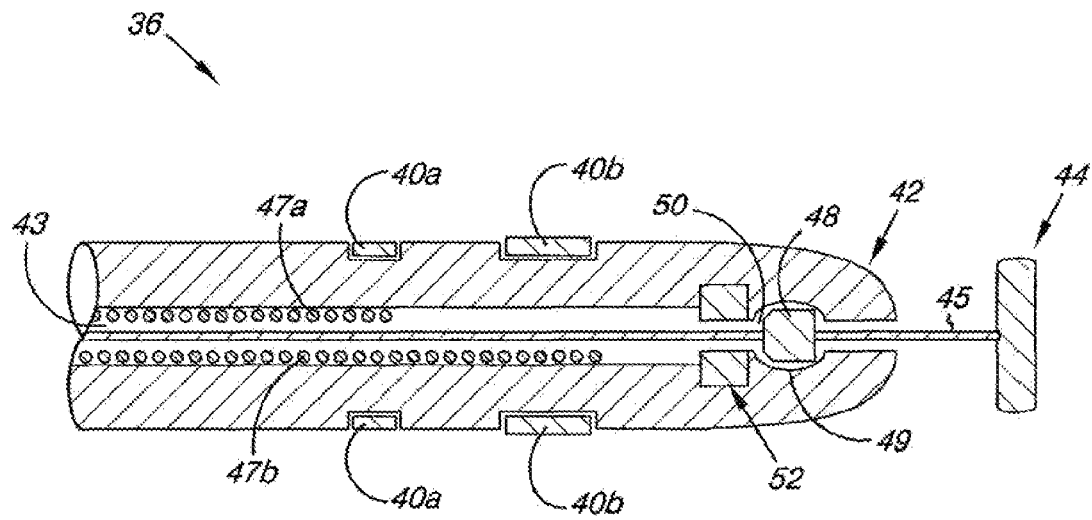
Fig. 2
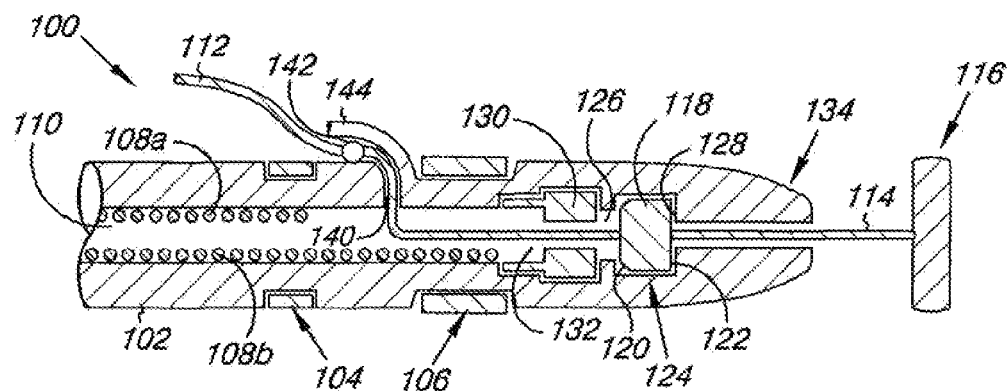
Fig. 3A
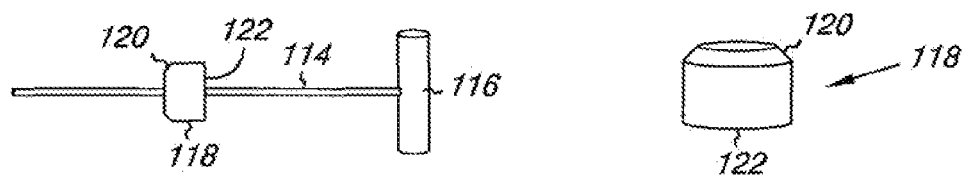
Fig. 3B
Fig. 3C

DISTAL OR PROXIMAL FIXATION OF OVER-THE-TETHER MYOCARDIAL LEADS

CROSS REFERENCES

The present application claims the benefit of the following U.S. Provisional Applications: Application Ser. No. 60/514,037 filed Oct. 24, 2003, entitled "Absorbable Myocardial Lead Fixation System", Application Ser. No. 60/514,665 filed Oct. 27, 2003, entitled "Lead Electrode Arrangement for Myocardial Leads", Application Ser. No. 60/514,042 filed Oct. 24, 2003, entitled "Tapered Tip for Myocardial Lead", Application Ser. No. 60/514,714 filed Oct. 27, 2003, entitled "Minimally-Invasive Fixation Systems for Over-the-Tether Myocardial Leads", Application Ser. No. 60/514,039 filed Oct. 24, 2003, entitled "Distal or Proximal Fixation of Over-the-Suture Myocardial Leads", Application Ser. No. 60/514,146 filed Oct. 24, 2003, entitled "Myocardial Lead with Fixation Mechanism", Application Ser. No. 60/514,038 filed Oct. 24, 2003, entitled "Delivery Instrument for Myocardial Lead Placement" and Application Ser. No. 60/514,713 filed Oct. 27, 2003, entitled "Drug-Eluting Myocardial Leads", all of which are incorporated herein by reference.

Reference is hereby made to commonly assigned U.S. patent application Ser. No. 10/821,421, filed Apr. 9, 2004 entitled "Cardiac Electrode Anchoring System" and the following commonly assigned U.S. patent applications filed on an even date herewith, all of which are incorporated herein by reference: application Ser. No. 10/972,049, entitled "Myocardial Lead," application Ser. No. 10/971,549, entitled "Myocardial Lead with Fixation Mechanism," application Ser. No. 10/971,551, entitled "Myocardial Lead Attachment System" and application Ser. No. 10/971,577, entitled "Absorbable Myocardial Lead Fixation System."

PARTIES TO A JOINT RESEARCH AGREEMENT

The present invention, as defined by the claims herein, was made by parties to a Joint Research Agreement between Cardiac Pacemakers, Inc. and Dr. Osypka, GmbH.

FIELD OF THE INVENTION

This invention relates generally to implantable lead assemblies for stimulating and/or sensing electrical signals in muscle tissue. More particularly, it relates to myocardially-implanted leads for cardiac stimulation.

BACKGROUND OF THE INVENTION

Cardiac rhythm management systems are used to treat heart arrhythmias. Pacemaker systems are commonly implanted in patients to treat bradycardia (i.e., abnormally slow heart rate). A pacemaker system includes an implantable pulse generator and leads, which form the electrical connection between the implantable pulse generator and the heart. An implantable cardioverter defibrillator ("ICD") is used to treat tachycardia (i.e., abnormally rapid heart rate). An ICD also includes a pulse generator and leads that deliver electrical energy to the heart.

The leads coupling the pulse generator to the cardiac muscle are commonly used for delivering an electrical pulse to the cardiac muscle, for sensing electrical signals produced in the cardiac muscle, or for both delivering and sensing. The leads are susceptible to categorization according to the type of connection they form with the heart. An endocardial lead includes at least one electrode at or near its distal tip adapted to contact the endocardium (i.e., the tissue lining the inside of the heart). An epicardial lead includes at least one electrode at or near its distal tip adapted to contact the epicardium (i.e., the tissue lining the outside of the heart). Finally, a myocardial lead includes at least one electrode at or near its distal tip inserted into the heart muscle or myocardium (i.e., the muscle sandwiched between the endocardium and epicardium). Some leads have multiple spaced apart distal electrodes at differing polarities and are known as bipolar type leads. The spacing between the electrodes can affect lead performance and the quality of the electrical signal delivered or sensed through the heart tissue.

The lead typically includes a flexible conductor surrounded by an insulating tube or sheath that extends from the electrode at the distal end to a connector pin at the proximal end. Endocardial leads are typically delivered transvenously to the right atrium or ventricle and commonly employ tines at a distal end for engaging the trabeculae.

The treatment of congestive heart failure ("CHF"), however, often requires left ventricular stimulation either alone or in conjunction with right ventricular stimulation. For example, cardiac resynchronization therapy ("CRT") (also commonly referred to as biventricular pacing) is an emerging treatment for heart failure, which requires stimulation of both the right and the left ventricle to increase cardiac output. Left ventricular stimulation requires placement of a lead in or on the left ventricle near the apex of the heart. One technique for left ventricular lead placement is to expose the heart by way of a thoracotomy. The lead is then positioned so that one or more electrodes contact the epicardium or are embedded in the myocardium. Another method is to advance an epicardial lead endovenously into the coronary sinus and then advance the lead through a lateral vein of the left ventricle. The electrodes are positioned to contact the epicardial surface of the left ventricle.

The left ventricle beats forcefully as it pumps oxygenated blood throughout the body. Repetitive beating of the heart, in combination with patient movement, can sometimes dislodge the lead from the myocardium. The electrodes may lose contact with the heart muscle, or spacing between electrodes may alter over time.

There is a need for an improved myocardial pacing lead suitable for chronic implantation and an attachment system for stabilizing such a lead in the heart.

SUMMARY OF THE INVENTION

According to one embodiment, the present invention is a myocardial lead attachment system for securing a lead within the myocardium. The attachment system includes an anchor configured to engage the heart, a tether coupled to the anchor and a lead body. The lead body has a proximal end, a distal end, a lumen for accepting the tether and a lock housing in the lumen. A lock structure is on the tether and mates with the lock housing and restrains motion of the lead with respect to the tether in either of a proximal or a distal direction.

According to another embodiment, the present invention is a myocardial lead attachment system for securing a lead within the myocardium. The attachment system includes an anchor configured to engage the heart, a tether coupled to the anchor and a lead body. The lead body has a proximal end, a distal end and a lumen for accepting the tether. The attachment system further includes a distal lock for engaging the tether to the distal end of the lead body. The distal lock includes a lock structure formed on a distal end of the tether and a lock housing in the lumen. The lock structure mates with the lock housing and restrains motion of the lead body with respect to the tether in either of a proximal or a distal direction. The attachment system further includes a proximal lock for engaging the tether to the lead body proximal to the distal lock. The proximal lock includes a through-hole extending from the lumen through the lead body at a location the same as or proximal to the lock housing for receiving a portion of the tether proximal to the distal lock and a second lock structure on the tether coupling the tether to the lead body adjacent the through-hole.

According to another embodiment, the present invention is a myocardial lead attachment system for securing a lead within the myocardium. The attachment system includes an anchor configured to engage the heart, a tether coupled to the anchor and a lead body. The lead body has a proximal end, a distal end and a lumen for accepting the tether. The attachment system further includes a distal lock for engaging the tether to the distal end of the lead body. The distal lock includes a lock structure formed on a distal end of the tether and a lock housing in the lumen. The lock structure mates with the lock housing and restrains motion of the lead body with respect to the tether in either of a proximal or a distal direction. The attachment system further includes a proximal lock formed on the tether and adapted to mate with the proximal end of the lead body. The proximal lock includes a second lock structure formed on the tether for fixing the tether in frictional engagement to the proximal end of the lead body.

According to another embodiment, the present invention is a method of securing a myocardial lead in the myocardium. An anchor coupled to a distal end of a tether is advanced through the myocardium to an implant location. A myocardial lead is threaded onto the tether. The lead is advanced over the tether to the implant location. A distal end of the lead is locked onto the distal end of the tether at a first attachment site. The tether is tensioned and the tether is secured to the lead at a second attachment site proximal to the first attachment site.

This summary is not intended to describe each embodiment or every implementation of the present invention. Advantages and a more complete understanding of the invention will become apparent upon review of the detailed description and claims in conjunction with the accompanying drawings.

BRIEF DESCRIPTION OF THE DRAWINGS

FIG. 2 is a sectional view of the distal portion of the myocardial lead attachment system of FIG. 1A according to one embodiment of the present invention.

FIG. 3A is a sectional view of a distal portion of a myocardial lead attachment system according to another embodiment of the present invention.

FIG. 3B is a side view of the tether of FIG. 3A.

FIG. 3C is a perspective view of the lock of FIG. 3A.

Figure 1A:
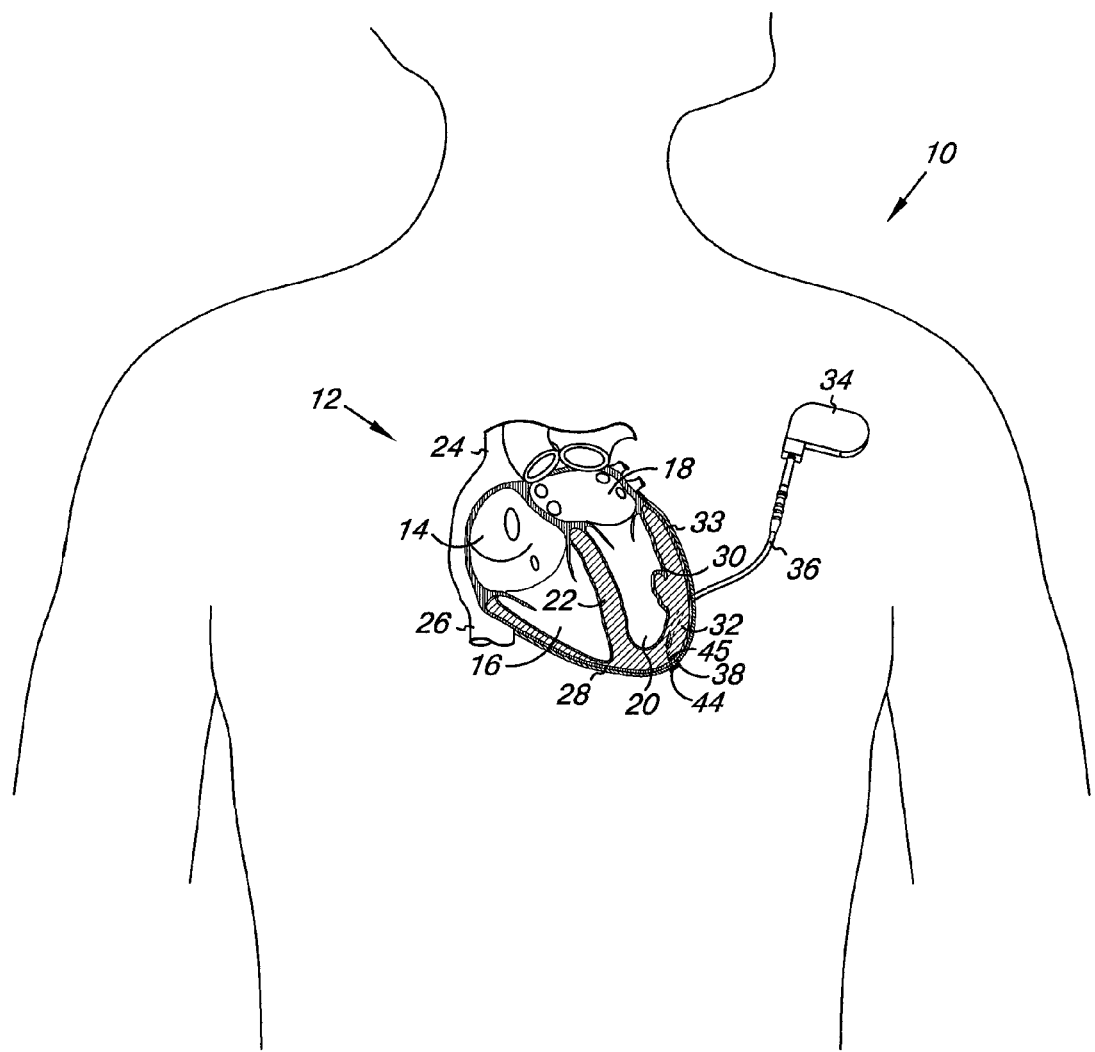
FIG. 1A is a sectional view of a portion of the vasculature and a myocardial lead attachment and pacing system according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1A is a sectional view of a pacing system 10 deployed in a human heart 12 according to one embodiment of the present invention. As shown in FIG. 1A, the heart 12 includes a right atrium 14 and a right ventricle 16 separated from a left atrium 18 and a left ventricle 20 by a septum 22. During normal operation of the heart 12, deoxygenated blood is fed into the right atrium 14 through the superior vena cava 24 and the inferior vena cava 26. The deoxygenated blood flows from the right atrium 14 into the right ventricle 16. The deoxygenated blood is pumped from the right ventricle 16 into the lungs, where the blood is re-oxygenated. From the lungs the oxygenated blood flows into the left atrium 18, then into the left ventricle 20. The left ventricle 20 beats forcefully to pump the oxygenated blood throughout the body.

The outer walls of the heart 12 are lined with a tissue known as the epicardium 28. The inner walls of the heart are lined with a tissue known as the endocardium 30. The heart muscle, or myocardium 32, is sandwiched between the endocardium 30 and the epicardium 28. A tough outer pericardial sac 33 surrounds the heart 12.

The pacing system 10 includes a pulse generator 34 coupled to a myocardial lead 36. The pulse generator 34 is typically implanted in a pocket formed underneath the skin of the patient's chest or abdominal region. The lead 36 extends from the pulse generator 34 to the heart 12 and is implanted in the myocardium 32 near an apex 38 of the heart 12. The lead 36 delivers electrical signals from the pulse generator 34 to an electrode on the lead 36 to accomplish pacing of the heart 12 (not visible in FIG. 1A). An anchor mechanism 44 is coupled to the lead 36 via a tether 45 to secure the lead 36 to the heart 12 and to retain the electrode in a chosen location.

Figure 1B:
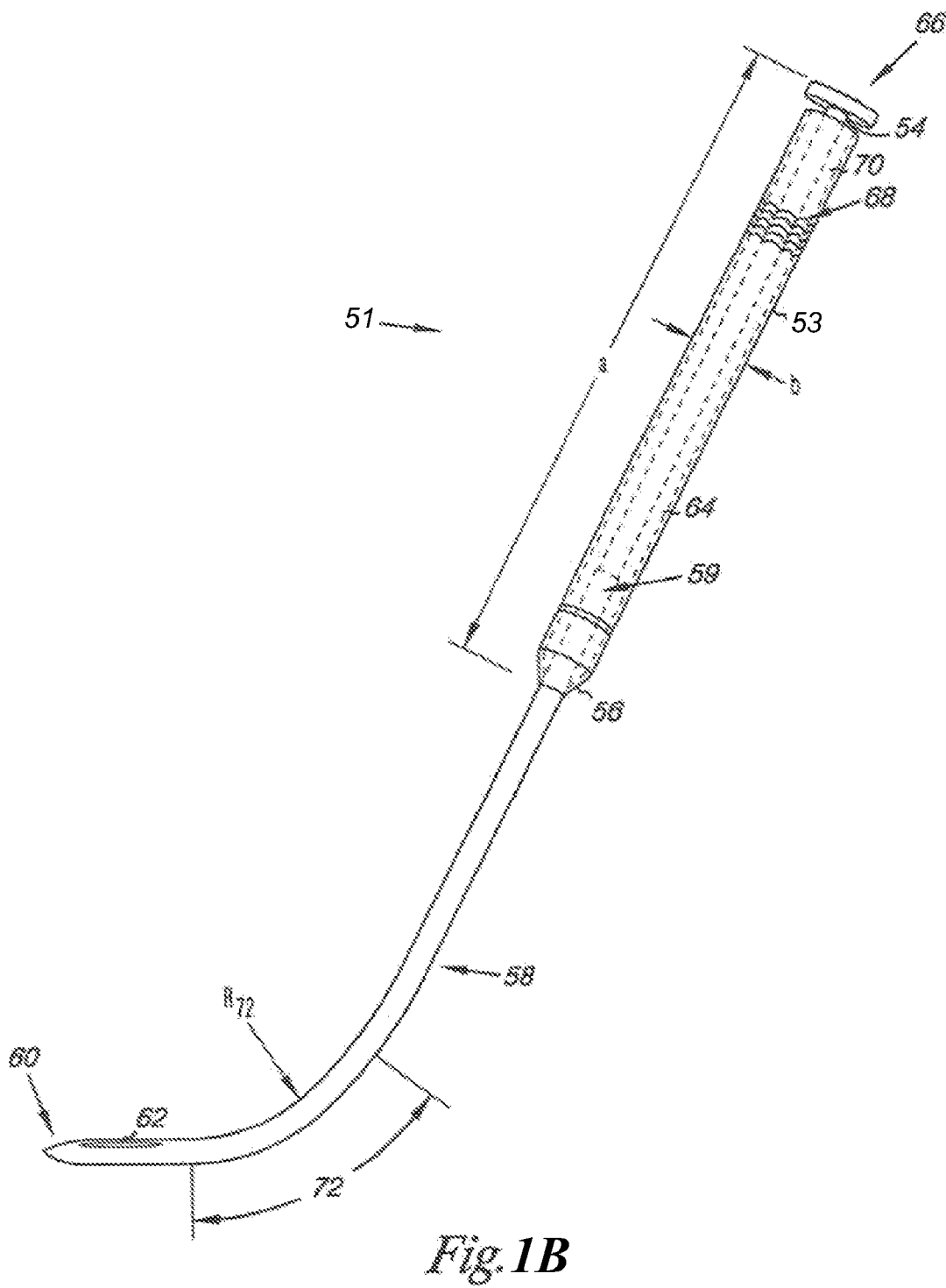
FIG. 1B is a side view of a delivery instrument for use in conjunction with the myocardial lead attachment system of FIG. 1A according to one embodiment of the present invention.

The lead 36 and anchor mechanism 44 may be implanted in the heart 12 via a delivery instrument and according to methods described in above-identified "Myocardial Lead Attachment System". Briefly, the delivery instrument is used to pierce the epicardium 30 and draw anchor mechanism 44 and the tether 45 through the myocardium 32. As the delivery instrument traverses the myocardium 32, it creates a tract (not visible in FIG. 1A) extending through the myocardial tissue 32. The anchor mechanism 44 is deployed, such that it engages the heart 12 at, for example, the epicardium 28. The delivery instrument is withdrawn back through the tract. The anchor mechanism 44 retains the tether 45 in place, resisting the force exerted on the tether 45 by the withdrawing delivery instrument. FIG. 1B shows a delivery instrument 51 according to one embodiment of the present invention. The delivery instrument 51 includes a needle portion 58 having a distal tip 60 and a nest 62. The nest 62 is sized to receive at least a portion of the anchor mechanism 44 (not visible in FIG. 1B). The delivery instrument 51 further includes an ejection mechanism 66 coupled to an actuator (not visible in FIG. 1B) for ejecting the anchor mechanism 44 from the nest 62. The delivery instrument 51 includes a handle 53 having a proximal end 54 and a distal end 56. The needle portion 58 is coupled to the handle 53 and extends from the distal end 56. The needle portion 58 is of a hypotube construction with an internal lumen 59. The handle 53 has an internal lumen 64 continuous with the needle lumen 59. The ejection mechanism 66 is located on the handle 53 and is operable within the internal lumen 64. According to other embodiments, the ejection mechanism 66 is located elsewhere on the handle 53.

After the delivery instrument is removed, the lead 36 is threaded onto the tether 45 and advanced over the tether 45 into the heart 12. The tether 45 is tensioned and coupled to the lead 36 to secure the lead 36 in a stable position.

FIG. 2 shows a distal portion of the myocardial lead attachment system 10. The lead 36 includes a pair of electrodes, a proximal anode 40a and a distal cathode 40b. A pair of coiled conductive members 47a and 47b extends longitudinally through the lead 36 and are electrically coupled to the anode 40a and the cathode 40b, respectively. The lead 36 has a lumen 43 extending longitudinally therethrough for receiving the tether 45. The tether 45 is provided with a distal lock for restraining motion of the lead 36 with respect to the tether 45 in either of a proximal or a distal direction. The distal lock includes a lock structure 48 formed on the tether. A distal end 42 of the lead 36 is provided with a lock housing 49 adapted to receive the lock 48. As the lead 36 is advanced over the tether 45, the distal tip 42 of the lead 36 approaches the lock 48. The distal tip 42 is resiliently deflectable such that the lock 48 is received in the lumen 43. The distal end 42 of the lead 36 advances slightly beyond the lock 48 until the lock 48 engages the lock housing 49. The lock 48 and lock housing 49 mate and form a locking arrangement that retains the lead 36 in a stable position in the myocardium 32. The locking arrangement is desirable because it helps to reduce migrations of the distal tip 42 of the lead body 36 due to contractions of the heart 12 and patient movement.

The lock arrangement can be any configuration that securely attaches the lead 36 to the tether 45. In the present embodiment, the lock housing 49 is a cavity 50 formed in the internal lumen 43 proximal to the distal tip 42 of the lead 36. A non-resilient internal ring 52 is positioned about the lumen 43 proximal to the cavity 50. The ring 52 has a diameter smaller than the size of the lock 48. While the distal tip 42 of the lead 36 is sufficiently resilient to expand and allow the lock 48 to enter the lead 36, the ring 52 does not deflect, and the lead 36 is prevented from advancing past the lock 48.

FIGS. 3A-3C show a distal portion of a myocardial lead attachment system 100 in accordance with another embodiment of the present invention. Myocardial lead attachment system 100 includes many of the features of the embodiment shown in FIG. 2, including a lead body 102 having a proximal anode 104 and a distal cathode 106, a pair of coiled conductive members 108a and 108b. The coiled conductive members 108a and 108b are coupled to the proximal anode 104 and distal cathode 106, respectively. The lead body 102 further includes an internal lumen 110 for receiving a tether 112. A distal end 114 of the tether 112 is coupled to an anchor mechanism 116. Shown more clearly in FIGS. 3B and 3C, a lock 118 is formed on the tether 112 near the distal end 114 and is shaped as a three-dimensional wedge. A forward face 120 of the lock 118 is ramped and pointed toward a proximal end of the tether 112 (not shown), while a trailing face 122 of the wedge-shaped lock 118 is generally perpendicular to the tether 112.

Returning to FIG. 3A, the lead 102 is provided with a cavity 124 forming a lock housing 126 in the lumen 110. The cavity 124 has a distal side 128 perpendicular to the length of the lead 102. A non-resilient ring 130 is positioned at a proximal side 132 of the lock housing 126. The lead 102 includes a through hole 140 extending from the lumen 110 through the lead body 102 proximal to the lock housing 126, near the location where the lead 102 exits the epicardium 28, and a flap or pocket 144 adjacent the through hole 140.

Figure 4:
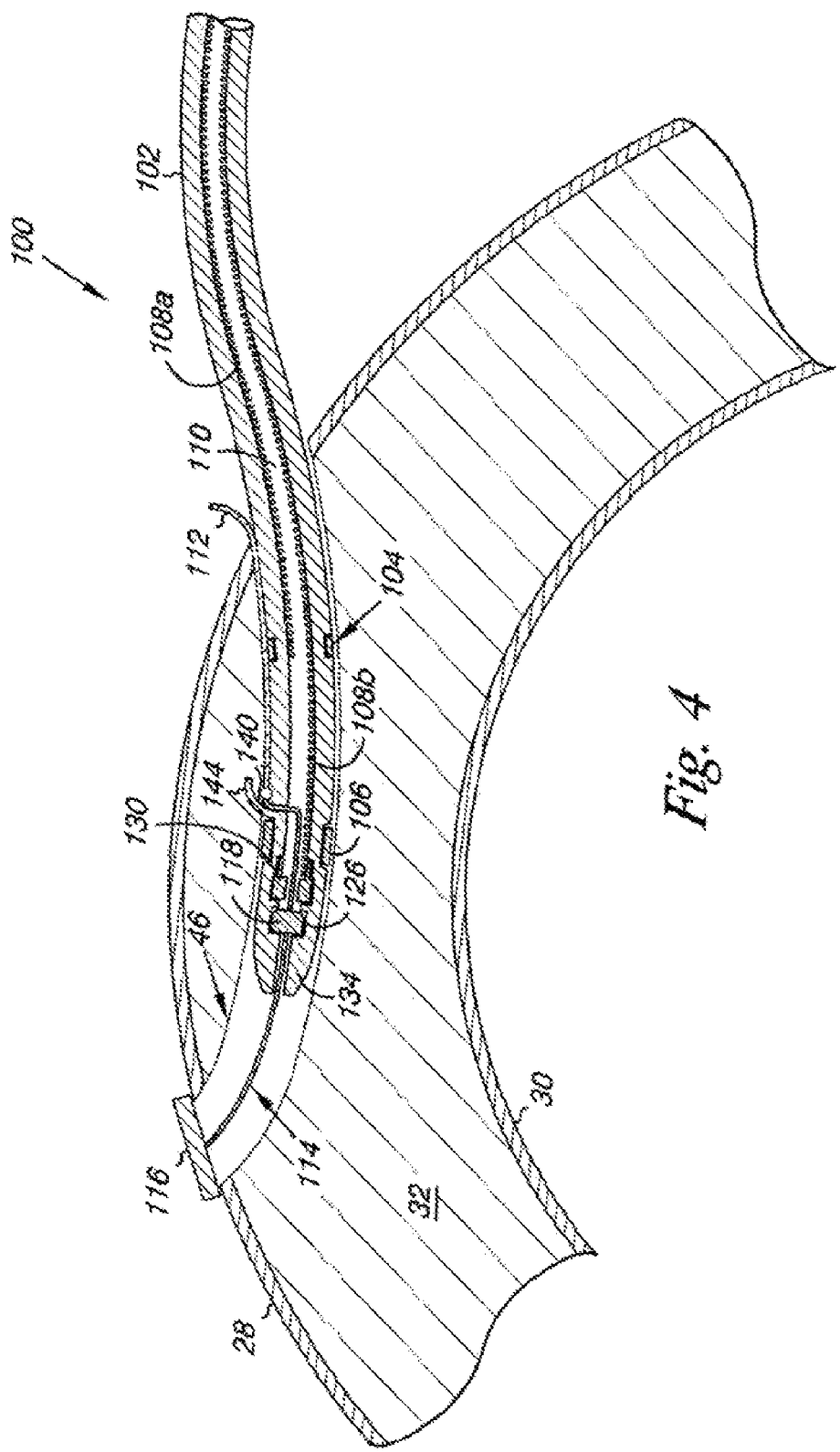
FIG. 4 is a sectional view of a distal portion of the myocardial lead attachment system of FIG. 3A implanted in the myocardium according to another embodiment of the present invention.

FIG. 4 shows a distal portion of the myocardial lead attachment system 100 implanted in the myocardium 32. Prior to lead implantation, the tether 112 is drawn out of the through hole 140. The lead body 102, now threaded onto the tether 112, is then advanced over the tether 112 through a tract 46 in the myocardium 32. As a distal tip 134 of the lead 102 advances to the wedge-shaped lock 118, the ramped side 120 of the wedge-shaped lock 118 deforms the distal tip 134 of the lead 102, allowing the lock 118 to enter and pass through the lumen 110 while the lead 102 continues to advance forward. The lock 118 encounters and mates with the lock housing 126, as the ring 130 prevents further distal advancement of the lead 102 beyond the lock 118. The tip 134 returns to its original shape due to its resilient nature. When the perpendicular side 128 of the lock housing 126 engages the lock perpendicular trailing face 122, further longitudinal sliding of the lead 102 in a proximal direction is prevented. Furthermore, lock 118, when retained in lock housing 126, substantially blocks the passage of any fluids into the lead lumen 110.

When the lead 102 has been properly positioned against the lock 118 such that the lock 118 is mated with in the lock housing 126, the tether 112 is placed under tension relative to the lead 102 by applying a tensile force to the portion of the tether 112 exiting through the through hole 140. The tensioned tether 112 is then fixed to the lead 102 at an attachment site near the through hole 140. In this manner, the myocardial lead 102 is fixed along the tether 112 between the lock 118 and the attachment site, which retains the lead 102 in a consistent position within the myocardium 32.

According to one embodiment, the tether 112 is fixed to the lead 102 by forming a knot 142 in the tensioned tether 112 just outside the through hole 140 (See FIG. 3A). The knot 142 is of a sufficient size to be retained outside of the through hole 140 even while under tension. The tensile force draws the knot 142 against the lead 102 to a stable, fixed position. Again, this configuration secures the lead 102 between the lock 118 and the knot 142 at the through hole 140. The knot 142 resides within the flap 144. This prevents irritation to the myocardial tract 46 that may be caused by movement or sliding of the knot 142 within the tract 46.

Figure 5:
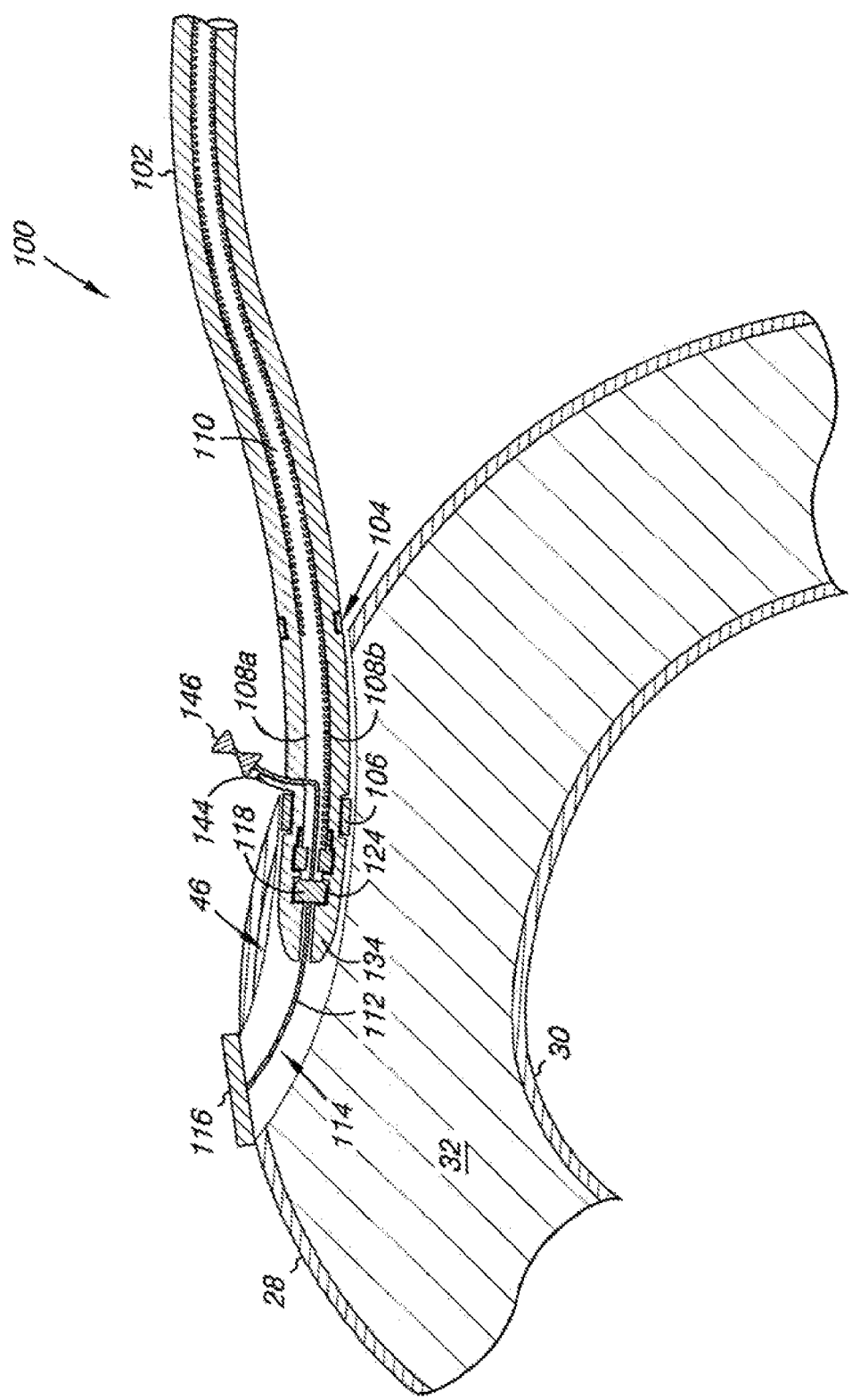
FIG. 5 is a sectional view of the distal portion of the myocardial lead attachment system of FIG. 3A implanted in the myocardium according to yet another embodiment of the present invention.

FIG. 5 shows another embodiment in which a slidable cinch 146 is positioned at the exit hole 140. The slidable cinch 146 is permanently attached, for example, by crimping, to the tether 112 to provide the desired tension on the lock 118 to hold the lead 102 in place. In all of these embodiments, once the fixation tension has been placed on the tether 112, the remaining tether 112 material can be cut and removed.

The lock structure 118 may take various shapes, and may be a separate member from the tether 112, for example a clip or other structure, fastened to the tether 112. In still other embodiments, the lock 118 and lock housing 126 may have other complementary mating shapes, which operate to inhibit motion of the lock 118 with respect to the lock housing 126.

Figure 6:
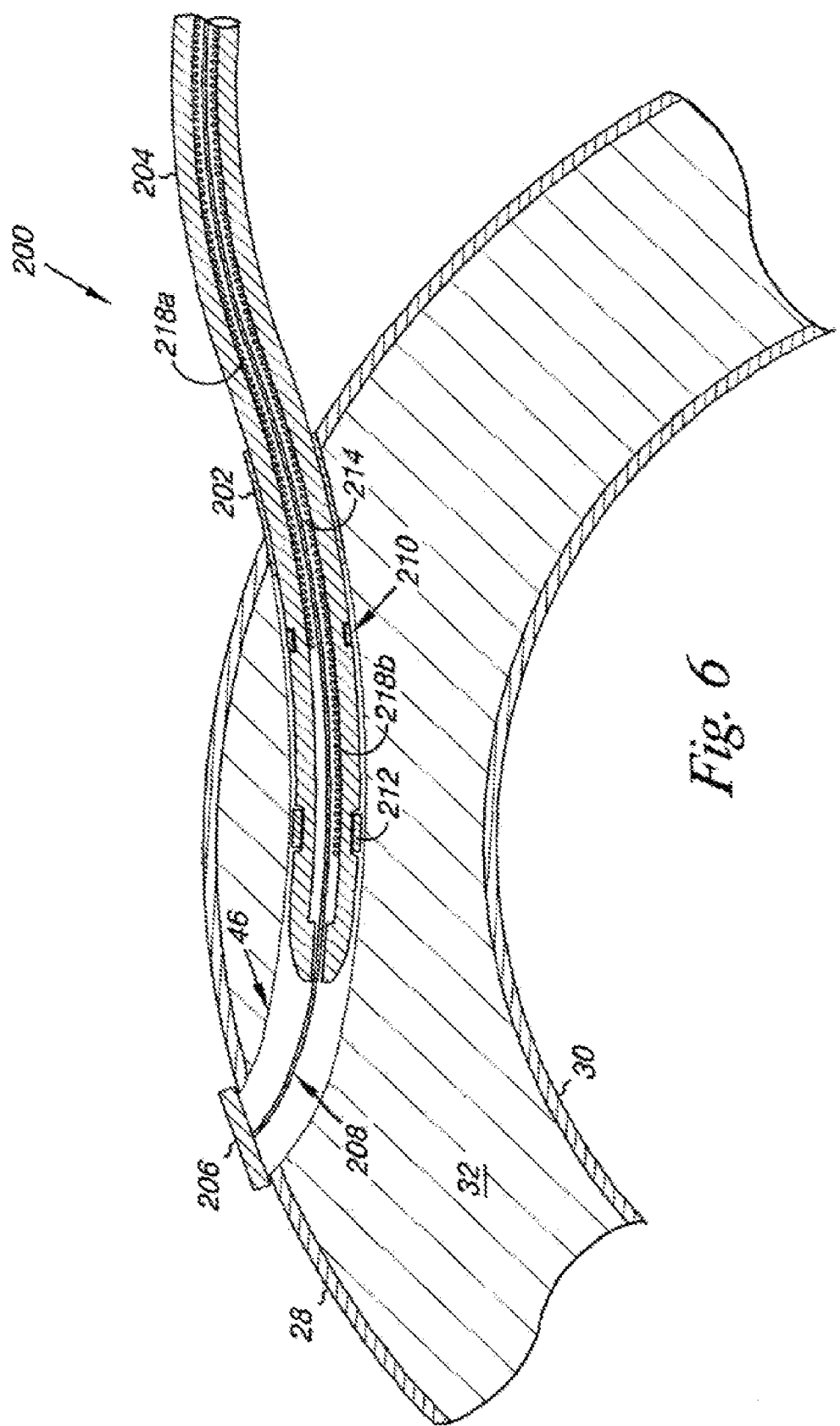
FIG. 6 is a sectional view of a distal portion of a myocardial lead attachment system implanted in the myocardium according to yet still another embodiment of the present invention.

FIG. 6 shows a distal portion of a myocardial lead attachment system 200 according to another embodiment of the present invention, including a distal lead fixation sleeve 202. The lead attachment system 200 includes a lead body 204, an anchor mechanism 206 and a tether 208 as previously described. The lead body 204 includes a proximal anode 210, a distal cathode 212 and a pair of coiled conductive members 218a and 218b as previously described, as well as an internal lumen 214 for receiving the tether 208. The anchor mechanism 206 and tether 208 are advanced through a tract 46 in the myocardium 32 as previously described. The lead body 204 is advanced over the tether 208. The fixation sleeve 202 is passed distally down the length of the lead 204 to the vicinity of the epicardium 28 exit site and partially inserted through the epicardium 28. The sleeve 202 is sutured into the epicardial tissue 28 to form a lock arrangement to restrain motion of the lead 204 with respect to the tether 208 in either of a proximal or a distal direction. The sleeve 202 may be stitched to the epicardial tissue 28 in such a way as to bring about sufficient compression on the lead body 204 to form a firm attachment at the exit site. The anchor 206 and tether 208 may be removed or may simply be left in place.

The preceding embodiments generally describe fixation systems for fixing the distal end of the lead in position. According to other embodiments of the present invention, proximal fixation systems are provided for fixing the proximal end of the lead in a selected position.

Figure 7A:
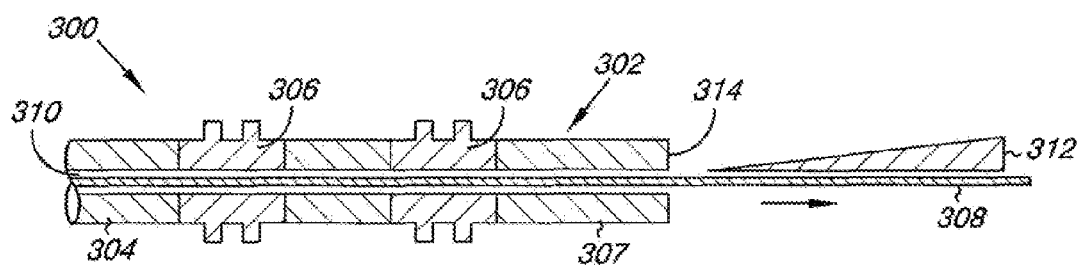
FIG. 7A is a sectional view of a proximal portion of a myocardial lead attachment system detailing a proximal lock in a first configuration according to one embodiment of the present invention.
Figure 7B:
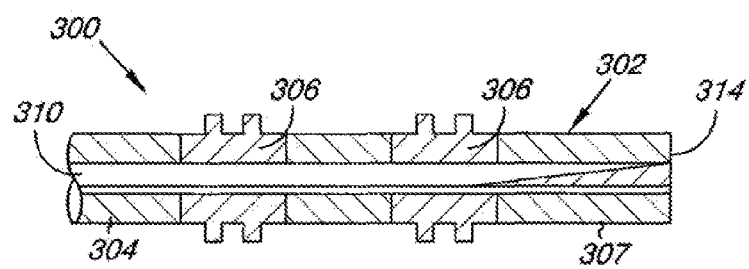
FIG. 7B is a sectional view of the myocardial lead attachment system of FIG. 7A showing the proximal lock in a second configuration.

FIGS. 7A-7B show a myocardial lead fixation system 300 according to another embodiment of the present invention. A proximal end 302 of a myocardial lead 304 is provided with a plurality of terminal connectors 306 for forming an electrical connection with a pacing device (not shown), and a proximal-most terminal pin 307. A tether 308 is coupled at a distal end to an anchor mechanism (not shown) and extends proximally through a lumen 310 in the lead 302 and terminal pin 307. The system 300 includes a lock structure 312 shaped like a wedge. After the lead 304 has been advanced over the tether 308 into the myocardial tract 46, the tether 308 is placed under tension relative to the lead 304. The lock structure 312 is inserted into the lumen 310 at the terminal pin 307, fixing the tether 308 in frictional engagement against an internal wall of the lumen 310 and forming a proximal locking arrangement to restrain motion of the lead 302 with respect to the tether 308 in either of a proximal or a distal direction. Any portion of the lock structure 312 may be cut along with the trailing length of the tether 308 flush against a proximal end 314 of the terminal pin 307. The terminal pin 307 and terminal connectors 306 may be inserted into the pulse generator 34 without interference from the proximal locking arrangement (See FIG. 1A).

Figure 8A:
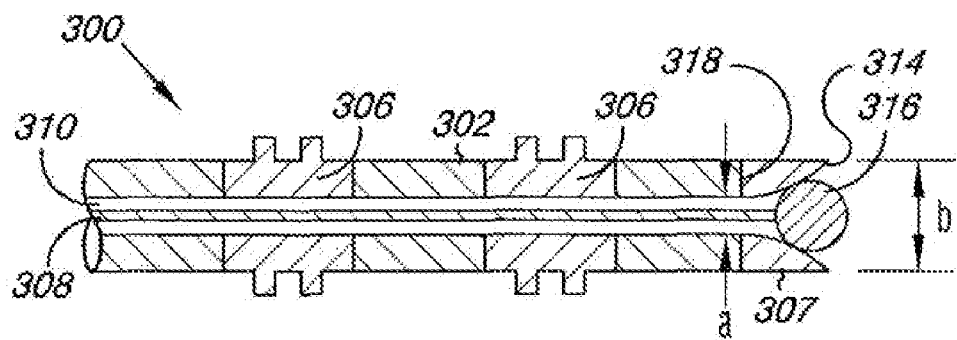
FIG. 8A is a sectional view of a proximal portion of a myocardial lead attachment system detailing a proximal lock according to one embodiment of the present invention.
Figure 8B:
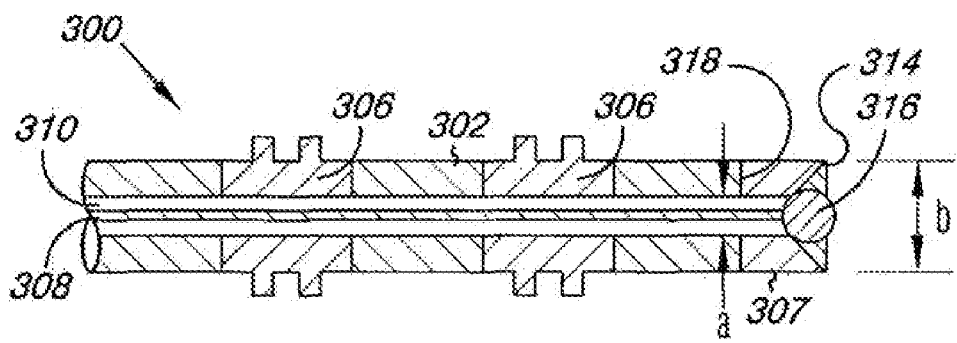
FIG. 8B is a sectional view of a proximal portion of a myocardial lead attachment system detailing a proximal lock according to another embodiment of the present invention.
Figure 8C:
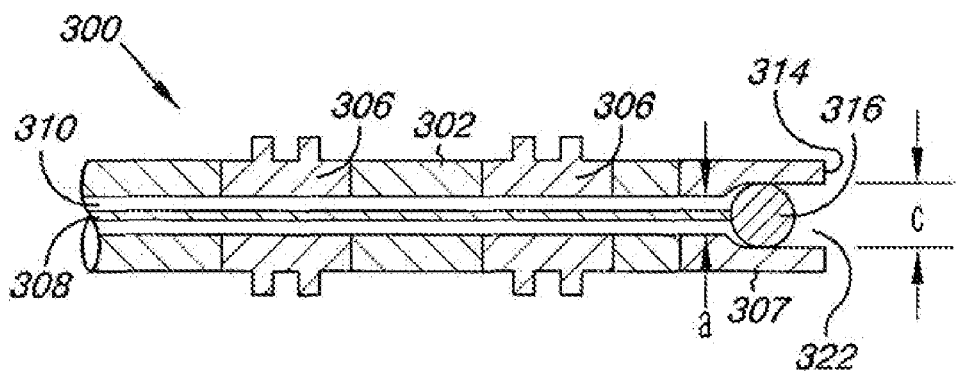
FIG. 8C is a sectional view of a proximal portion of a myocardial lead attachment system detailing a proximal lock according to still another embodiment of the present invention.

FIGS. 8A-8C show additional embodiments of proximal locking arrangements in which in place of the wedge-shaped lock structure 312, a knot 316 or other mechanical stop is formed on the tether 312 of a size sufficient to be retained in frictional engagement with the lead 302 outside of the lumen 310. The tether 308 is tensioned and the knot 316 is formed to restrain motion of the lead body 302 with respect to the tether 308 in either of a proximal or a distal direction. As with respect to the embodiment shown in FIGS. 7A and 7B, it is important that the proximal locking arrangement not interfere with insertion of the terminal pin 307 into the pulse generator 34.

According to one embodiment, as shown in FIG. 8A, the lumen 310 tapers outwardly proximally to form a housing to receive the knot 316. At a mid region 318 of the terminal pin 307, approximately 0.024 inches distal to a proximal tip 314 of the terminal pin 307, the wall of the terminal pin 307 is about 0.029 inches thick and the lumen 310 has an internal diameter a of about 0.022 inches. The lumen 310 tapers outwardly such that at the proximal tip 314 the lumen 310 has an internal diameter b of about 0.050 inches and the wall of the terminal pin 307 is about 0.010 inches thick. According to one embodiment, a single knot 316 of the tether 308 is able to be concealed within the lumen 310 but is yet of a size to be prevented from sliding longitudinally within the lumen 310 beyond the mid region 318.

FIG. 8B shows another embodiment, in which the lumen 310 angles outwardly at about 45° from the mid region 318 to the proximal tip 314. The internal diameter a of the lumen 310 at the mid region 318 is about 0.024 inches. The internal diameter b of the lumen 310 at the proximal tip 314 is about 0.045 inches. According to one embodiment, a single knot 316 of the tether 308 protrudes approximately 0.020 inches from the distal end 320 of the terminal pin 307. According to yet another embodiment, the internal diameter a of the lumen 310 at the mid region 318 is about 0.0197 inches and the internal diameter b of the lumen 310 at the proximal tip 314 is about 0.0315 inches.

FIG. 8C shows another embodiment, in which the lumen 310 is chamfered at an angle of about 45° distal to the proximal tip 314. The lumen 310 angles outwardly; forming a housing 322 having an internal diameter c greater than the internal diameter of the lumen 310. According to one embodiment, the internal diameter a of the lumen 310 is about 0.0210 inches and the lumen 310 angles outwardly at about 45° for about 0.012 inches. The internal diameter c of the housing 322 is about 0.045 inches, and extends about 0.040 inches to the distal tip 320. According to one embodiment, a single knot 316 of the tether 308 is able to be concealed within the housing 322.

According to one embodiment, the tether 308 is formed of 0.0095 inch diameter polypropylene and a single knot 316 of the tether 308 is about 0.040 inches long by about 0.030 inches wide.

Figure 9:
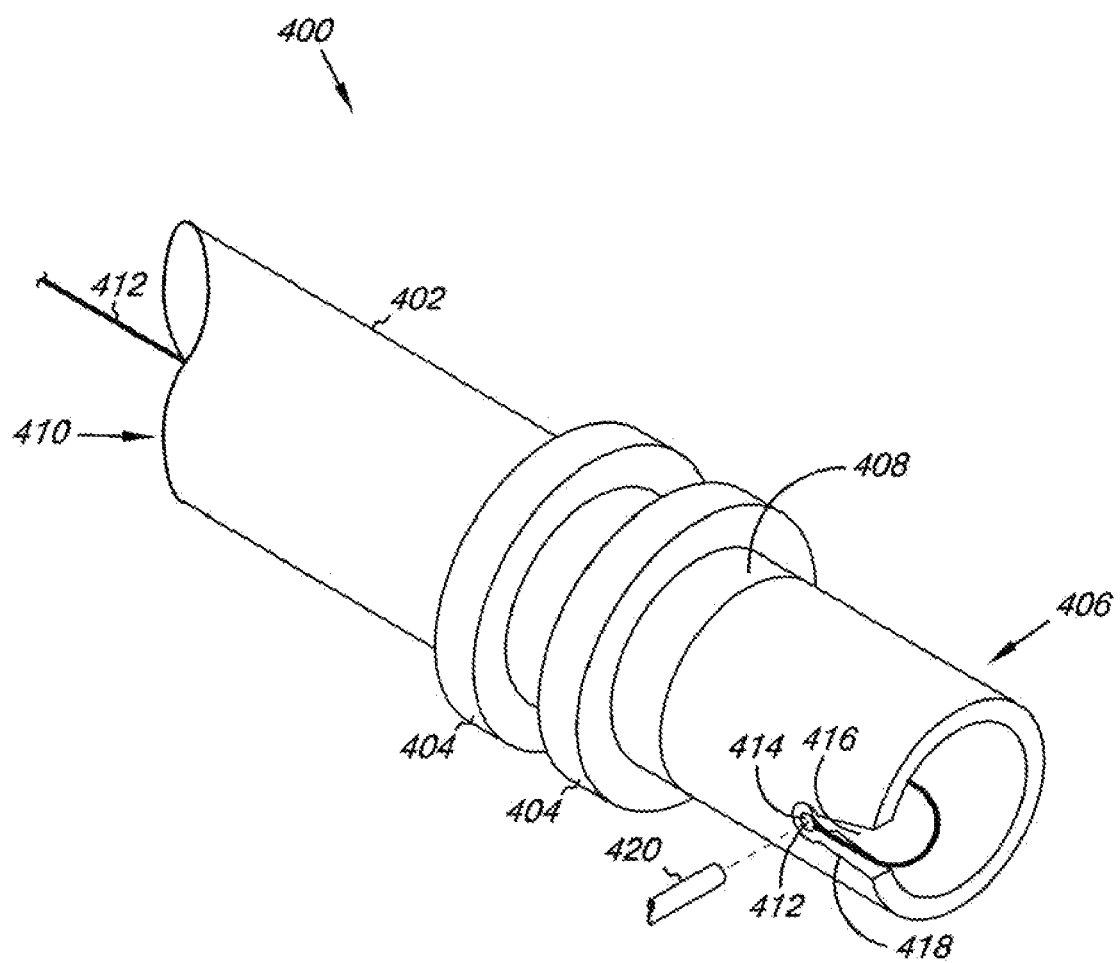
FIG. 9 is a perspective view of a proximal portion of a myocardial lead attachment system according to another embodiment of the present invention.

FIG. 9 is a perspective view of a proximal locking arrangement at a proximal portion of a myocardial lead attachment system 400, according to one embodiment of the present invention. The system 400 includes a lead body 402 having a terminal connector 404 and a terminal pin 406 positioned at a proximal end 408 of the lead 402. A lumen 410 extends through the lead body 402 and terminal pin 406 for receiving a tether 412. The terminal pin 406 of the lead 402 includes a tether lock pin 414 at a proximal end 408 of the lead 402. The lock pin 414 includes a first channel 416 through which the tether 412 passes. The lock pin 414 also includes a side groove 418 into which the tether 412 is placed under slight tension. Once so positioned, an insert pin 420 is inserted into the lock pin 414 and firmly pressed forward. The insert pin 420 fixes the tether 412 at the lock pin 414. In one embodiment, the insert pin 420 also operates to cut the excess length of the tether 412.

According to one embodiment, both a distal and a proximal attachment system are used to secure the lead to the tether. The combination of a proximal locking arrangement and a distal locking arrangement stabilize the lead within the heart 12 and reduce the likelihood of migrations of the lead from the implant site. Furthermore, the lead can be positioned in the heart 12 in a variety of configurations, including epicardial-epicardial, as is shown in the preceding figures, or epicardial-endocardial, intra-myocardial and pericardial-pericardial, as is described in above-identified application entitled "Myocardial Lead Attachment System."

Various modifications and additions can be made to the exemplary embodiments discussed without departing from the scope of the present invention. Accordingly, the scope of the present invention is intended to embrace all such alternative, modifications, and variations as fall within the scope of the claims, together with all equivalents thereof.

We claim:

1. A myocardial lead attachment system for securing a lead within the myocardium, the system comprising:
    an anchor configured to advance in a first orientation, rotate to a second orientation, and anchor against an epicardial surface in the second orientation, wherein the anchor is configured to be generally parallel to the epicardial surface in the second orientation;
    a tether coupled to the anchor, the tether having a proximal end and a distal end;
    a lead body having:
        a proximal end and a distal end, and
        a lumen for accepting the tether configured such that the lead body can be threaded over the proximal end of the tether and slideably advanced over the tether toward the anchor during implantation;
    wherein the tether extends out the distal end of the lead body;
    a distal lock for engaging the tether to the distal end of the lead body, the distal lock comprising:
        a lock structure formed on a distal end of the tether, and
        a lock housing in the lumen, wherein the lock structure mates with the lock housing and restrains motion of the lead body with respect to the tether in either of a proximal or a distal direction; and
    a proximal lock restraining longitudinal motion of the tether with respect to the lead body.

2. A myocardial lead attachment system for securing a lead within the myocardium, the system comprising:
    an anchor configured to advance in a first orientation, rotate to a second orientation generally parallel to an epicardial surface, and anchor against the epicardial surface in the second orientation;
    a tether coupled to the anchor, the tether having a proximal end, a distal end, and a lock structure; and
    a lead body having:
        a proximal end and a distal end,
        a lumen for accepting the tether configured such that the lead body can be threaded over the proximal end of the tether and slideably advanced over the tether toward the anchor during implantation, and
        a lock housing in the lumen, wherein the lock structure mates with the lock housing and restrains motion of the lead body with respect to the tether in either of a proximal or a distal direction;
    wherein the tether extends out the distal end of the lead body.

3. The system of claim 2 wherein the tether further includes a proximal lock adapted to mate with the proximal end of the lead body, such that the lead body is restrained from longitudinal motion with respect to the tether.

4. The system of claim 3 wherein the proximal lock is a knot tied in the tether and sized larger than a diameter of the lumen.

5. The system of claim 4 wherein a proximal portion of the lumen tapers outwardly to receive the knot.

6. The system of claim 4 wherein a proximal portion of the lumen angles outwardly to receive the knot.

7. The system of claim 4 wherein a proximal portion of the lumen is chamfered to form a proximal region having a first diameter that is sized to receive the knot and a distal region having a second diameter that is sized to prevent entry of the knot further into the lumen.

8. The system of claim 3 wherein the proximal lock is a wedge inserted into the lead lumen at the proximal end of the lead body in frictional engagement with the tether.

9. The system of claim 3 wherein the proximal lock comprises:
    a lock pin at the proximal end of the lead body, the lock pin having a first channel for receiving the tether and a side groove for receiving the tether under tension; and
    an insert pin received in the lock pin for retaining the tether under tension.

10. The system of claim 2 further comprising:
    a through-hole extending from the lumen through the lead body at a location the same as or proximal to the housing for receiving a portion of the tether proximal to the lock structure; and
    a second lock structure on the tether coupling the tether to the lead body adjacent the through-hole.

11. The system of claim 10 wherein the second lock structure is a knot tied in the tether.

12. The system of claim 10 wherein the second lock structure is a slidable cinch crimped onto the tether.

13. The system of claim 10 wherein the lead body further includes a pocket for receiving the second lock structure.

14. The system of claim 2 wherein the lock structure has a diameter greater than a diameter of the lumen and wherein at least a portion of the lead body is resiliently deflectable to accept the lock structure into the lumen and return to an undeflected state when the lock structure is advanced into the lock housing.

15. The system of claim 2 wherein the lock structure is generally shaped as a wedge having an angled leading face and a trailing face extending perpendicular to the tether.

16. The system of claim 2 wherein the lock structure is a knot tied in the tether.

* * * * *

UNITED STATES PATENT AND TRADEMARK OFFICE
CERTIFICATE OF CORRECTION

PATENT NO. : 7,499,759 B2  
APPLICATION NO. : 10/972298  
DATED : March 3, 2009  
INVENTOR(S) : M. Sean Coe et al.

It is certified that error appears in the above-identified patent and that said Letters Patent is hereby corrected as shown below:

On the Title Page, Item (56) References Cited, Foreign Patent Documents, page 2
Delete "EP   1000834   5/2000" and replace it with -- EP   1000634   5/2000 --

Signed and Sealed this

Fifteenth Day of September, 2009

David J. Kappos  
*Director of the United States Patent and Trademark Office*